(12) United States Patent
Singleton et al.

(10) Patent No.: US 9,241,484 B2
(45) Date of Patent: *Jan. 26, 2016

(54) COMPOSITIONS OF DIBROMOMALONAMIDE AND THEIR USE AS BIOCIDES

(75) Inventors: Freddie L. Singleton, Vernon Hills, IL (US); Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/007,485

(22) PCT Filed: Mar. 12, 2012

(86) PCT No.: PCT/US2012/028701
§ 371 (c)(1),
(2), (4) Date: Sep. 25, 2013

(87) PCT Pub. No.: WO2012/134790
PCT Pub. Date: Oct. 4, 2012

(65) Prior Publication Data
US 2014/0023727 A1   Jan. 23, 2014

Related U.S. Application Data

(60) Provisional application No. 61/467,414, filed on Mar. 25, 2011.

(51) Int. Cl.
*A01N 37/18* (2006.01)
*A01N 37/30* (2006.01)
*A01N 43/50* (2006.01)
*A01N 59/00* (2006.01)
*C02F 1/50* (2006.01)
*C02F 1/76* (2006.01)
*C11D 3/32* (2006.01)
*C11D 3/395* (2006.01)
*C11D 3/48* (2006.01)

(52) U.S. Cl.
CPC ............. *A01N 37/18* (2013.01); *A01N 37/30* (2013.01); *A01N 43/50* (2013.01); *A01N 59/00* (2013.01); *C02F 1/50* (2013.01); *C02F 1/76* (2013.01); *C11D 3/32* (2013.01); *C11D 3/3951* (2013.01); *C11D 3/3956* (2013.01); *C11D 3/48* (2013.01)

(58) Field of Classification Search
None
See application file for complete search history.

(56) References Cited

U.S. PATENT DOCUMENTS

| 4,241,080 A * | 12/1980 | Burk ............................ 514/528 |
| RE39,021 E | 3/2006 | Sweeny |
| 7,407,590 B2 | 8/2008 | Ludensky et al. |
| 2009/0117202 A1* | 5/2009 | Feldman et al. ............. 424/613 |
| 2010/0314316 A1* | 12/2010 | Yin et al. ...................... 210/636 |
| 2012/0177745 A1* | 7/2012 | Singleton et al. ............ 424/616 |

* cited by examiner

*Primary Examiner* — Robert A Wax
*Assistant Examiner* — Danah Al-Awadi
(74) *Attorney, Agent, or Firm* — Tifani M. Edwards

(57) ABSTRACT

A biocidal composition comprising 2,2-dibromomalonamide and an oxidizing biocide, and its use for the control of microorganisms in aqueous and water-containing systems.

7 Claims, No Drawings

COMPOSITIONS OF DIBROMOMALONAMIDE AND THEIR USE AS BIOCIDES

CROSS-REFERENCE TO RELATED APPLICATIONS

This application claims priority from provisional application Ser. No. 61/467,414, filed Mar. 25, 2011, which is incorporated herein by reference in its entirety.

FIELD OF THE INVENTION

The invention relates to biocidal compositions and methods of their use for the control of microorganisms in aqueous and water-containing systems. The compositions comprise 2,2-dibromomalonamide and an oxidizing biocide.

BACKGROUND OF THE INVENTION

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and an oxidizing biocide comprising hypochlorous acid or a salt thereof, monohalodimethylhydantoin, dichlorodimethylhydantoin, or dibromodimethylhydantoin.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and an oxidizing biocide comprising hypochlorous acid or a salt thereof, monohalodimethylhydantoin, dichlorodimethylhydantoin, or dibromodimethylhydantoin. It has surprisingly been discovered that combinations of 2,2-dibromomalonamide and the oxidizing biocide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The term "2,2-dibromomalonamide" refers to a compound represented by the following chemical formula:

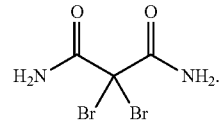

Unless otherwise indicated, the ratios, percentages, parts, and the like used herein are by weight and numeric ranges are inclusive of the numbers defining the range.

In some embodiments of the invention, the weight ratio of 2,2-dibromomalonamide to the oxidizing biocide is between 16:1 and 1:8.

In some embodiments, the composition of the invention comprises 2,2-dibromomalonamide and hypochlorous acid or a salt thereof, such as sodium hypochlorite. The 2,2-dibromomalonamide and the hypochlorous acid or hypochlorite are commercially available and/or can be readily prepared by those skilled in the art using well known techniques. Hypochlorite may, for instance, be in the form of commercial bleach (e.g., Clorox®) or more concentrated commercial grades (e.g., 15%) that may typically be used in industrial applications. Hypochlorite may also be electrolytically generated.

In some embodiments, the weight ratio of 2,2-dibromomalonamide to hypochlorous acid or a salt thereof is between 16:1 and 1:1.

In a still further embodiment, the composition of the invention comprises 2,2-dibromomalonamide and monohalodimethylhydantoin. Examples of suitable monohalodimethylhydantoin include monochlorodimethylhydantoin and monobromodimethylhydantoin, with monochlorodimethylhydantoin being preferred. The materials can be easily prepared by those skilled in the art. Monochlorodimethylhydantoin may be prepared, for instance, by reacting dimethylhydantoin with hypochlorous acid at a 1:1 molar ratio. The monohalodimethylhydantoin may be pre-prepared prior to addition to the aqueous system or it may be generated in situ.

In some embodiments, the weight ratio of 2,2-dibromomalonamide to monohalodimethylhydantoin is between 1:1 and 1:4.

In another embodiment, the composition of the invention comprises 2,2-dibromomalonamide and dichlorodimethylhydantoin. Dichlorodimethylhydantoin may be prepared, for instance, by reacting dimethylhydantoin with hypochlorous acid at a 1:2 molar ratio. The dichlorodimethylhydantoin may be pre-prepared prior to addition to the aqueous system or it may be generated in situ.

In some embodiments, the weight ratio of 2,2-dibromomalonamide to dichlorodimethylhydantoin is between 16:1 and 1:2.

In a further embodiment, the composition of the invention comprises 2,2-dibromomalonamide and dibromodimethylhydantoin. Dibromodimethylhydantoin may be prepared, for instance, by reacting dimethylhydantoin with hypobromous acid at a 1:2 molar ratio. The dibromodimethylhydantoin may be pre-prepared prior to addition to the aqueous system or it may be generated in situ.

In some embodiments, the weight ratio of 2,2-dibromomalonamide to dibromodimethylhydantoin is between 16:1 and 1:8.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g., oilfield water, pulp and paper water, cooling water), oil and gas field injection water, produced water, other oil and gas functional fluids such as drilling muds and fracturing fluids, fluids for use in oil and gas field transportation pipelines, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and an oxidizing biocide) is typically at least 1 ppm, alternatively at least 3 ppm, alternatively at least 7 ppm, alternatively at least 10 ppm, alternatively at least 30 ppm, or alternatively at least 100 ppm based on the total weight of the aqueous or water containing system. In some embodiments, a suitable upper limit for the actives concentration is 1000 ppm, alternatively 500 ppm, alternatively 100 ppm, alternatively 50 ppm, alternatively 30 ppm, alternatively 15 ppm, alternatively 10 ppm, or alternatively 7 ppm, based on the total weight of the aqueous or water containing system.

The components of the composition can be added to the aqueous or water containing system separately, or preblended prior to addition. In addition, the oxidizing biocides may be generated in situ in the aqueous or water containing system. A person of ordinary skill in the art can easily determine the appropriate method of addition and/or generation. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope.

EXAMPLES

The results provided in the Examples are generated using a growth inhibition assay. Details of each assay are provided below.

Growth Inhibition Assay. The growth inhibition assay used in the Examples measures inhibition of growth (or lack thereof) of a microbial consortium Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3.6H_2O$ (1); $CaCl_2.2H_2O$ (10); $MgSO_4.7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 µl quantities to sterile microtiter plate wells. Dilutions of 2,2-dibromomalonamide ("DBMAL") and/or "Biocide B" are then added to the microtiter plate. After preparing the combinations of actives as illustrated below, each well is inoculated with 100 µl of a cell suspension containing ca. $1 \times 10^6$ cells per milliliter of a mixture of *Pseudomonas aeruginosa*, *Klebsiella pneumoniae*, *Staphylococcus aureus*, and *Bacillus subtilis*. The final total volume of medium in each well is 300 µl. Once prepared as described herein, the concentration of each active ranges from 25 ppm to 0.195 ppm as illustrated in Table 1. The resulting matrix allows testing of eight concentrations of each active and 64 combinations of actives in the ratios (of actives).

TABLE 1

Template for microtiter plate-based synergy assay showing concentrations of each active. Ratios are based on weight (ppm) of each active.

| | | DBMAL (ppm) | | | | | | | |
|---|---|---|---|---|---|---|---|---|---|
| | | 25.000 | 12.500 | 6.250 | 3.125 | 1.563 | 0.781 | 0.391 | 0.195 |
| Biocide | 25.000 | 1:1 | 1:2 | 1:4 | 1:8 | 1:16 | 1:32 | 1:64 | 1:128 |
| B (ppm) | 12.500 | 2:1 | 1 | 1:2 | 1:4 | 1:8 | 1:16 | 1:32 | 1:64 |

TABLE 1-continued

Template for microtiter plate-based synergy assay showing concentrations of each active. Ratios are based on weight (ppm) of each active.

| | DBMAL (ppm) | | | | | | | |
|---|---|---|---|---|---|---|---|---|
| | 25.000 | 12.500 | 6.250 | 3.125 | 1.563 | 0.781 | 0.391 | 0.195 |
| 6.250 | 4:1 | 2:1 | 1 | 1:2 | 1:4 | 1:8 | 1:16 | 1:32 |
| 3.125 | 8:1 | 4:1 | 2:1 | 1 | 1:2 | 1:4 | 1:8 | 1:16 |
| 1.563 | 16:1 | 8:1 | 4:1 | 2:1 | 1 | 1:2 | 1:4 | 1:8 |
| 0.781 | 32:1 | 16:1 | 8:1 | 4:1 | 2:1 | 1 | 1:2 | 1:4 |
| 0.391 | 64:1 | 32:1 | 16:1 | 8:1 | 4:1 | 2:1 | 1 | 1:2 |
| 0.195 | 128:1 | 64:1 | 32:1 | 16:1 | 8:1 | 4:1 | 2:1 | 1:1 |

Controls (not shown) contain the medium with no biocide added.

Immediately after the microtiter plates are prepared, the optical density (OD) readings for each well is measured at 580 nm and the plates are then incubated at 37° C. for 24 hr. After the incubation period, the plates are gently agitated before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

$$\text{Synergy Index} = M_{DBMAL}/C_{DBMAL} + M_B/C_B$$

where $C_{DBMAL}$: Concentration of DBMAL required to inhibit ≥90% of bacterial growth when used alone $C_B$: Concentration of biocide (B) required to inhibit ≥90% of bacterial growth when used alone.

$M_{DBMAL}$: Concentration of DBMAL required to inhibit ≥90% of bacterial growth when used in combination with biocide (B).

$M_B$: Concentration of biocide (B) required to inhibit ≥90% of bacterial growth when used in combination with DBMAL The SI values are interpreted as follows:

SI<1: Synergistic combination
SI=1: Additive combination
SI>1: Antagonistic combination In the Examples below, the amounts of biocides in the solution are measured in mg per liter of solution (mg/l). Since solution densities are approximately 1.00, the mg/l measurement corresponds to weight and can be expressed as parts per million (ppm). Both units may therefore be used interchangeably in the Examples.

Example 1

DBMAL and Hypochlorous Acid

Cell suspensions are challenged with DBMAL, hypochlorous acid (HOCl), and combinations of DBMAL and HOCl. Percent inhibition of growth values are calculated as described above and used to determine the minimum concentration of each active and combinations of actives to result in at least 90% inhibition of growth ($I_{90}$ values). The $I_{90}$ values for DBMAL and HOCl are 6.25 mg/l and 0.78 mg/l, respectively. Several combinations of DBMAL and HOCl in which the concentration of each active is less than the respective $I_{90}$ value result in >90% inhibition of growth. Table 2 contains ratios and synergy index values for the synergistic combinations.

TABLE 2

Ratios and synergy index values of synergistic combinations of DBMAL and HOCl.

| DBMAL (mg/l) | HOCl (mg/l) | DBMAL:HOCl Ratio | Synergy Index (SI) |
|---|---|---|---|
| 1.56 | 0.39 | 4:1 | 0.75 |
| 0.78 | 0.39 | 2:1 | 0.63 |
| 0.39 | 0.39 | 1:1 | 0.56 |
| 3.13 | 0.195 | 16:1 | 0.75 |
| 1.56 | 0.195 | 8:1 | 0.5 |
| 0.78 | 0.195 | 4:1 | 0.37 |
| 0.39 | 0.195 | 2:1 | 0.31 |

Example 2

DBMAL and Monochlorodimethylhydantoin

In this example, DBMAL is evaluated for synergy with monochlorodimethylhydantoin (MCDMH) prepared by reacting dimethylhydantoin (DMH) with HOCl in a 1:1 molar ratio Immediately before the assay is performed, solutions of DMH and HOCl are combined to provide equimolar concentrations of each reactant. The resulting monochlorinated hydantoin, MCDMH, is used in the assay. The $I_{90}$ values for DBMAL and MCDMH are 6.25 mg/l and 3.13 mg/l, respectively. Some combinations of DBMAL and MCDMH cause >90% inhibition of growth when used in concentrations less than the respective $I_{90}$ concentrations. Combinations of DBMAL and MCDMH found to be synergistic are shown in Table 3.

TABLE 3

Synergistic ratios and SI values for DBMAL + MCDMH combinations

| DBMAL (mg/l) | MCDMH (mg/l) | DBMAL:MCDMH Ratio | SI |
|---|---|---|---|
| 1.56 | 1.56 | 1:1 | 0.75 |
| 0.78 | 1.56 | 1:2 | 0.62 |
| 0.39 | 1.56 | 1:4 | 0.56 |

Example 3

DBMAL and Dichlorodimethylhydantoin

In this example, DBMAL was tested alone and in combination dichlorodimethylhydantoin DCDMH) prepared by reacting with DHM with HOCl in a 1:2 molar ratio. The $I_{90}$ values for DBMAL and DCDMH are 6.25 mg/l and 0.78 mg/l, respectively. Table 4 contains synergistic ratios and synergy index values for combinations of the two actives.

TABLE 4

Synergistic ratios and SI values for DBMAL and DCDMH.

| DBMAL (mg/l) | DCDMH (mg/l) | DBMAL:DCDMH Ratio | Synergy Index (SI) |
|---|---|---|---|
| 1.56 | 0.39 | 4:1 | 0.75 |
| 0.78 | 0.39 | 2:1 | 0.625 |
| 0.39 | 0.39 | 1:1 | 0.56 |
| 0.195 | 0.39 | 1:2 | 0.53 |
| 3.13 | 0.195 | 16:1 | 0.75 |

Example 4

DBMAL and Dibromodimethylhydantoin

In this example, DMH is reacted with HOBr (formed by combining equimolar ratios of NaBr and HOCl) in a 1:2 molar ratio to form dibromodimethylhydantoin (DBDMH). The $I_{90}$ values for DBMAL and DBDMH are 6.25 mg/l and 3.13 mg/l, respectively. HOBr has an $I_{90}$ value of 12.5 mg/l. Several combinations of the two actives are synergistic as shown in Table 5.

TABLE 5

Synergistic ratios and SI values for DBMAL and DBDMH.

| DBMAL (mg/l) | DBDMH (mg/l) | DBMAL:DBDMH Ratio | Synergy Index (SI) |
|---|---|---|---|
| 1.56 | 1.56 | 1:1 | 0.75 |
| 0.78 | 1.56 | 1:2 | 0.62 |
| 0.39 | 1.56 | 1:4 | 0.56 |
| 0.195 | 1.56 | 1:8 | 0.53 |
| 3.13 | 0.78 | 4:1 | 0.75 |
| 1.56 | 0.78 | 2:1 | 0.5 |
| 0.78 | 0.78 | 1:1 | 0.375 |
| 0.39 | 0.78 | 1:2 | 0.31 |
| 3.13 | 0.39 | 8:1 | 0.625 |
| 3.13 | 0.195 | 16:1 | 0.56 |

What is claimed is:

1. A synergistic biocidal composition comprising: 2,2-dibromomalonamide and an oxidizing biocide consisting of hypochlorous acid or a salt thereof, monohatodimethylhydantoin, dichlorodimethythydantoin, and dibromodimethylhydantoin wherein the weight ratio of 2,2-dibromomalonamide to the oxidizing biocide is between 16:1 and 1:8.

2. A composition according to claim 1 wherein the oxidizing biocide comprises a monohalodimethyihydantoin and the weight ratio of the 2,2-dibromomalonamide to the monohalodimethylhydantoin is between 1:1 and 1:4.

3. A composition according to claim 1 wherein the oxidizing comprises dichlorodimethythydantoin and the weight ratio of the 2,2-dibromonialonamide to the diehlorodimethythydantoin is between 16:1 and 1:2.

4. A composition according to claim 1 wherein the oxidizing biocide comprises dibromodimethylhydantoin and the weight ratio of the 2,2-dibromomalonamide to the dibromodimethylhydantoin is between 16:1 and 1:8.

5. A composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oil and gas field injection water, produced water, oil and gas functional fluid, drilling mud, fracturing fluid, fluid in oil and gas field transportation pipeline, fuel, air washer, wastewater, ballast water, filtration systems, swimming pool or spa water.

6. A method for controlling microorganism growth in an aqueous or water-containing system, the method comprising treating the aqueous or water-containing system with an effective amount of a composition according to claim 1.

7. A method according to claim 6 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oil and gas field injection water, produced water, oil and gas functional fluid, drilling mud, fracturing fluid, fluid in oil and gas field transportation pipleline, fuel, air washer, wastewater, ballast water, filtration system, swimming pool or spa water.

* * * * *